US008764672B2

(12) United States Patent
Manwaring et al.

(10) Patent No.: US 8,764,672 B2
(45) Date of Patent: Jul. 1, 2014

(54) SYSTEM, METHOD AND DEVICE FOR MONITORING THE CONDITION OF AN INTERNAL ORGAN

(76) Inventors: Preston K. Manwaring, Lebanon, NH (US); Ryan J. Halter, Orford, NH (US); Kim H. Manwaring, Phoenix, AZ (US)

(*) Notice: Subject to any disclaimer, the term of this patent is extended or adjusted under 35 U.S.C. 154(b) by 631 days.

(21) Appl. No.: 12/706,696

(22) Filed: Feb. 16, 2010

(65) Prior Publication Data

US 2010/0210958 A1 Aug. 19, 2010

Related U.S. Application Data

(60) Provisional application No. 61/207,613, filed on Feb. 17, 2009.

(51) Int. Cl.
*A61B 5/02* (2006.01)
*A61B 5/00* (2006.01)

(52) U.S. Cl.
USPC .......................................... 600/506; 600/561

(58) Field of Classification Search
USPC ................. 600/504–507, 544–545, 547–561; 324/600–727
See application file for complete search history.

(56) References Cited

U.S. PATENT DOCUMENTS

| 4,617,939 | A | | 10/1986 | Brown et al. |
| 4,893,630 | A | * | 1/1990 | Bray, Jr. ......................... 600/484 |
| 5,544,662 | A | | 8/1996 | Saulnier et al. |
| 5,746,214 | A | | 5/1998 | Brown et al. |
| 5,807,270 | A | | 9/1998 | Williams |
| 5,916,171 | A | | 6/1999 | Mayevsky |
| 5,919,142 | A | | 7/1999 | Boone et al. |

(Continued)

FOREIGN PATENT DOCUMENTS

| DE | 102007013367 A1 | 9/2008 |
| GB | 2 156 997 | 10/1985 |

(Continued)

OTHER PUBLICATIONS

Brown, et al, "Applied Potential Tomography: Possible Clinical Applications", "Clin. Phys. Physiol. Meas.", Feb. 26, 1985, pp. 109-121, vol. 6, No. 2, Publisher: The Institute of Physics.

(Continued)

*Primary Examiner* — Michael D'Angelo
*Assistant Examiner* — Tiffany Weston
(74) *Attorney, Agent, or Firm* — Loginov & Sicard; Keri E. Sicard; William A. Loginov

(57) ABSTRACT

A system, method and device for monitoring the condition of an internal organ, such as a brain, by providing an internal electrode. The internal electrode is operatively connected to at least one surface, external, electrode, and a system handler. A signal is generated between the electrodes such that the electrical properties, including conductivity and impedance among others, can be measured at and across the electrodes. The electrode arrangement allows for continuous monitoring of an internal organ and, where desired, mapping of the electrical properties thereof. The system obtains pressure readings, nodal conductivity and/or electrode impedance to monitor, map and report the condition of the internal organ. A correlation procedure is provided for generating a graphical representation of the condition of an internal organ from the gathered data. A medical treatment method is also provided for monitoring the status of the brain, and includes providing an internal electrode for measuring electrical properties of the internal organ.

17 Claims, 13 Drawing Sheets

(56) References Cited

U.S. PATENT DOCUMENTS

| | | | |
|---|---|---|---|
| 6,328,694 | B1 | 12/2001 | Michaeli |
| 6,360,123 | B1 * | 3/2002 | Kimchi et al. ............... 600/547 |
| 6,560,486 | B1 | 5/2003 | Osorio et al. |
| 6,887,199 | B2 | 5/2005 | Bridger et al. |
| 6,916,294 | B2 | 7/2005 | Ayad |
| 6,931,274 | B2 | 8/2005 | Williams |
| 6,950,699 | B1 | 9/2005 | Manwaring et al. |
| 2002/0095087 | A1 | 7/2002 | Mourad et al. |
| 2004/0030258 | A1 | 2/2004 | Williams et al. |
| 2004/0133120 | A1 * | 7/2004 | Frei et al. ............... 600/544 |
| 2004/0167385 | A1 | 8/2004 | Rioux et al. |
| 2006/0047201 | A1 | 3/2006 | Eide |
| 2007/0161891 | A1 | 7/2007 | Moore et al. |
| 2007/0161919 | A1 * | 7/2007 | DiLorenzo ............... 600/544 |
| 2007/0287899 | A1 | 12/2007 | Poupko et al. |

FOREIGN PATENT DOCUMENTS

| | | | |
|---|---|---|---|
| WO | WO 9724981 | 7/1997 | |
| WO | WO 03053234 A2 | 7/2003 | |
| WO | WO 2007022292 A2 | 2/2007 | |
| WO | WO 2008/005440 * | 1/2008 | ............... A61B 5/07 |
| WO | WO 2008005440 A2 | 1/2008 | |

OTHER PUBLICATIONS

Holder, et al., "Assessment and Calibration of a Low-Frequency System for Electrical Impedance Tomography (EIT), Optimized for Use in IMA", "Annals New York Academy of Sciences".

Bodo, et al., "Changes in the Intracranial Rheoencephalogram at Lower Limit of Cerebral Blood Flow Autoregulation", "Physiological Measurement", Jan. 26, 2005, pp. S1-S17, vol. 26, Publisher: Institute of Physics Publishing.

Robertson, et al, "Clinical Experience With a Continuous Monitor of Intracranial Compliance", "Journal of Neurosurgery", Nov. 1989, pp. 673-680, vol. 71.

Marmarou, et al., "Compartmental Analysis of Compliance and Outflow Resistance of the Cerebrospinal Fluid System", "Journal of Neurosurgery", Nov. 1975, pp. 523-534, vol. 43.

Czosnyka, et al., "Continuous Assessment of the Cerebral Vasomotor Reactivity in Head Injury", "Web of Science", , Publisher: Williams & Wilkins.

Kiening, et al., "Continuous Monitoring of Intracranial Compliance After Severe Head Injury: Relation to Data Quality, Intracranial Press", "British Journal of Neurosurgery", Aug. 2003, p. 311-318, vol. 17, No. 4, Publisher: Taylor & Francis healthsciences.

Sadleier, et al., "Detection of Intraventricular Blood Using EIT in a Neonatal Piglet Model", "31st Annual International Conference of IEEE EMBS", Sep. 2, 2009, pp. 3169-3172, Publisher: IEEE.

Tidswell, et al., "Electrical Impedance Tomography of Human Brain Activity With a Two-Dimensional Ring of Scalp Electrodes", "Physiological Measurement", 2001, pp. 167-175, vol. 22, Publisher: Institute of Physics Publishing Ltd.

Holder, et al., "Imaging of Physiologically Evoked Responses by Electrical Impedance Tomography With Cortical Electrodes in the Anaesthet", "Physiol. Meas.", 1996, pp. A179-A186, vol. 17, Publisher: IOP Publishing Ltd.

Egnor, et al., "A Model of Pulsations in Communicating Hydocephalus", "Pediatric Neurosurgery", Feb. 25, 2002, pp. 281-303, vol. 36, Publisher: S. Karger AG, Basel.

Vajkoczy, et al., "Continuous Monitoring of Regional Cerebral Blood Flow: Experimental and Clinical Validation of a Novel Thermal Diffusio", "Journal of Neurosurgery", Aug. 2000, pp. 265-274, vol. 93.

* cited by examiner

SYSTEM, METHOD AND DEVICE FOR MONITORING THE CONDITION OF AN INTERNAL ORGAN

RELATED APPLICATIONS

This application claims the benefit of U.S. Provisional Patent Application Ser. No. 61/207,613, filed Feb. 17, 2009, entitled Device and Method for Continuous Monitoring, Mapping and Display of Brain Compliance or Cerebral Elastography, the entire disclosure of which is herein incorporated by reference.

STATEMENT REGARDING FEDERALLY SPONSORED RESEARCH OR DEVELOPMENT

This invention was made in association with U.S. government support under Funding Agreement Numbers CA080139 and CA124925, awarded by the National Institutes of Health (NIH), EIR#2021601-08-0006. The government may have certain rights in this invention.

FIELD OF THE INVENTION

The present invention relates to monitoring and treating an internal organ that is injured, or has certain conditions or diseases. More particularly, the present invention relates to treatments and monitoring of brain injuries, conditions and diseases.

BACKGROUND OF THE INVENTION

Head trauma represents a spectrum of injury ranging from concussion through contusion, diffuse axonal injury, penetrating injury, and disruption of blood vessels with intracranial hemorrhage, as well as other brain conditions and diseases. These traumatic brain events lead to brain swelling as a result of evolving edema and threaten the sufficiency of blood flow to the brain, leading to further hypoxic-ischemic injury. This increased swelling manifests itself in a changing brain compliance (or conversely cerebral elastance) and can be represented as the relationship between intra-cranial pressure (ICP) and pulsatile regional cerebral blood flow (rCBF) waveforms. Certain conditions, or disease states, manifest a risk for "secondary injury" after the primary insult in the form of increased water volume content (swelling) which can be referred to as cerebral edema. These include head trauma, hydrocephalus, stroke, and brain tumor among others. Therefore, a significant aspect of management of clinical deterioration in these conditions is the monitoring of brain edema and treatment in an effort to minimize its harmful effects. Beyond head trauma, similar alterations in cerebral perfusion and ICP can follow in other pathologic conditions afflicting the brain such as hydrocephalus, stroke, brain tumor, and seizures.

Due to cranial constraint upon the swelling brain, intracranial pressure (ICP) may quickly deteriorate as the brain herniates across internal openings of the cranium such as the tentorium or the foramen magnum at its base. ICP increases in an exponential-like pattern within increasing intra-cranial volume in the form of brain edema, CSF, or blood. This relationship is referred to as the pressure-volume index (PVI). As the PVI deteriorates, the stiffness of the brain worsens, a condition called poor brain compliance, or its inverse, abnormal brain elastance. A goal of therapy is to identify and reverse worsening brain compliance within best potentials of aggressive therapy. The cranium is occasionally partially removed to give the brain more room to swell during the acute secondary injury phase. In addition to ICP monitoring, the clinician observes in order to recognize regional brain edema and its advancing pattern, influencing the therapeutic decision process. Frequent imaging using prior techniques is not optimal or practical management due to the risks to the patient of transport and the exposure of irradiation.

In an effort to improve early detection, and therefore treatment, of the patient with risk of increasing cerebral edema, multiple attempts have been explored. Portable CT scanners have been developed which eliminate the need of transport of the patient from the intensive care unit (ICU) to the radiology department. However, the method is still intermittent and is associated with increasing radiation dose.

Well recognized imaging modalities of human tissues can also be employed, such as Magnetic Resonance Imaging (MRI) and Ultrasound (US). However, MRIs are relatively impractical for use in acute TBI assessment because it does not image bone well and data acquisition is lengthy. Also, the static magnetic or changing RF fields used for imaging severely limit existing transducer and ventilator devices due to encumbrance or risk for burns or induced electrical currents into tissues.

Traumatic brain injuries require monitoring, as the ICP can increase and the cerebral perfusion can be altered into harmful range as a result of the injury or other condition. Uncontrolled intracranial pressure can result in irreversible damage, or even death. Existing systems lack the ability to continuously monitor brain compliance. Single snapshots of the state of the brain are not sufficient if damage is indicated in the initial scan, or if clinical status worsens. It is, therefore, desirable to provide a system that continuously monitors a patient by continuously mapping a brain image and displaying brain compliance. Furthermore, recognition of worsening injuries may be accomplished by continuously monitoring intra-cranial pressure and blood flow, as opposed to single snapshot views.

Additionally, external sensors have been applied in prior attempts to measure the electrical properties within a brain. However, this does not provide an accurate reading of the electrical properties, because only the surface or superficial region of the cerebrum is addressed. The signals generated by and between the electrodes are not capable of fully penetrating an internal organ to accurately portray its condition via monitoring and mapping its electrical properties. There is a need for a system that continuously and accurately monitors an internal organ such as a brain, or another internal organ, so as to provide the condition of the internal organ.

SUMMARY OF THE INVENTION

A system, method and device for monitoring the status of an internal organ, such as the brain, by examining the electrical properties of the internal organ is provided. In accordance with an illustrative embodiment, the system includes at least one central electrode integral with a pressure sensor or External Ventricular Drain (EVD), or alternatively can be provided as an additional electrode. The central, internal electrode is disposed within the internal organ and is in communication with at least one external, or surface electrode, to determine the electrical properties of a particular internal organ. A plurality of surface electrodes are provided to monitor the internal organ. The electrode arrangement allows for continuous monitoring of the internal organ and, where desired, mapping of the electrical properties thereof. These electrical properties can include impedance, conductivity, or other blood flow, pressure and volume measurements. The system obtains electrode readings and pressure measurements to monitor, map and report the condition of the internal organ. The properties can be reported to a physician in the form of a display with a scaling scheme, such as Green/Yellow/Red. The scaling scheme is indicative of the status and condition of the particular internal organ being analyzed. This provides a continuous monitoring and status reporting of the status of the internal organ.

The electrodes are operatively connected to a system handler, such as instrumentation or a system server that receives the measurement of signals generated between the electrodes, to monitor the status of an internal organ. The system handler includes a mapping application and a scoring application. The mapping application gathers information from the electrodes to generate a tomographic image and a map, or other graphical representation, of the status of the particular internal organ. The scoring application provides a score of the status of the particular internal organ. The score can be based on a scale of Green-Yellow-Red to indicate the condition of the internal organ. For instance, green is a normal condition for the internal organ, yellow is a worsening condition for the internal organ, and red is a severely damaged, or worst case scenario condition for the internal organ. This provides a physician with important real-time conditions to determine if intervention is necessary and proper.

A medical treatment method is also provided for monitoring the status of the brain or another internal organ. The medical treatment method comprises the steps of introducing an intra-cranial (or otherwise organ-adjacent) electrode, monitoring blood flow and ICP, and generating a framework, in the form of a graphical representation, to provide results of the electrical properties, and thereby the condition of the internal organ. The step of introducing an intra-cranial electrode can be performed by providing an intra-cranial catheter in communication with a plurality of surface electrodes to monitor and map the electrical properties and ICP of the brain.

BRIEF DESCRIPTION OF THE DRAWINGS

The invention description below refers to the accompanying drawings, of which.

DETAILED DESCRIPTION

There is provided a system, method and device for monitoring, mapping and otherwise reporting the status of electrical properties of an internal organ. The status is determined by examining electrical properties that represent the overall condition of the internal organ. The electrical properties can include conductivity, impedance, or any other quantifiable or measurable electrical property. Conductivity is a measurement of the ease at which current flows between two locations, and can be gauged to determine the flow of a substance, such as blood, within an internal organ. Impedance ('Z') is the ratio of voltage to current ($\Delta Z = \Delta V / \Delta I$). Impedance is a complex-valued number (real and imaginary components) that can change in both magnitude and phase as the frequency excitation current or voltage is swept from a low to high value. The resultant spectral signature can be very specific to tissue types and injuries and can also be mapped in three dimensions through an inverse problem. While the system is shown and described according to an exemplary brain implementation in FIGS. 1-7, it is highly and readily applicable to any internal organ for monitoring its condition or compliance. For example, the teachings are illustrated and described with respect to an alternate tracheal or carotid artery flow monitoring environment in FIG. 10.

Figure 1:
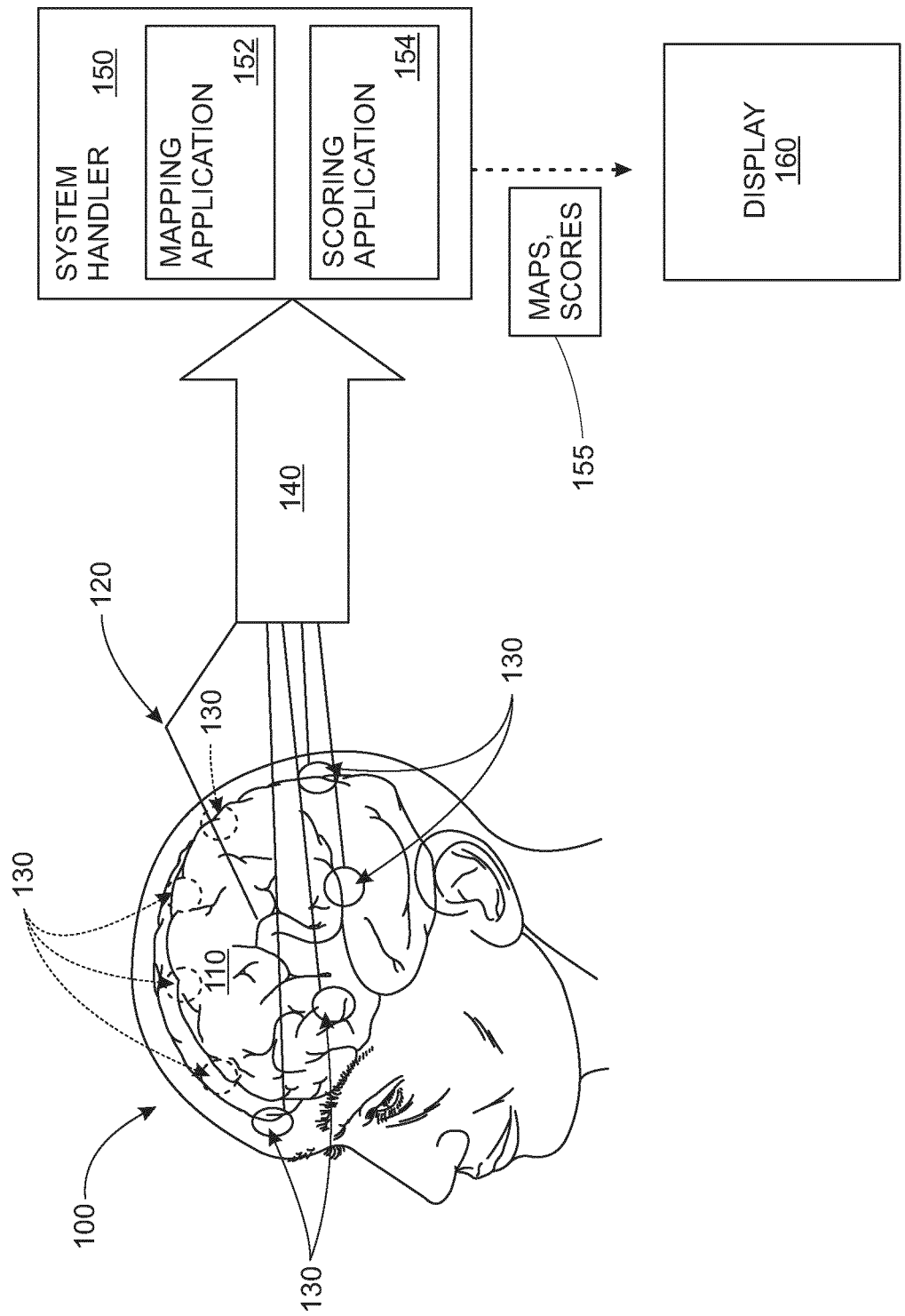
FIG. 1 is a schematic overview block diagram of a system for monitoring the status of a brain, according to an illustrative embodiment.

FIG. 1 shows an exemplary system 100 for monitoring a brain 110, according to an illustrative embodiment described herein. The system includes a central, intra-cranial catheter 120 that includes at least one central electrode (not explicitly shown). A plurality of central electrodes (such as depth or grid electrodes) can also be employed, or a single catheter having a plurality of electrodes disposed thereon. The catheter 120 is in communication with a plurality of external scalp electrodes 130. As depicted, each surface electrode is operatively connected (arrow 140) to a system handler 150. In this embodiment, there are eight external electrodes depicted (four in phantom). However, any number of external electrodes can be provided, ranging from a single external electrode (see FIG. 6A) to a plurality of external electrodes (see FIGS. 6B and 6C). The electrodes can, in an illustrative embodiment, each be independently wired directly to the handler (as depicted in FIG. 1), or can be otherwise appropriately inter-connected to generate and receive signals between the electrodes. The arrangement and circuitry used to implement the plurality of surface electrodes in communication with a central electrode is highly variable and should be readily apparent to those of ordinary skill.

The system handler 150 can comprise any appropriate computing system or server environment, or other appropriate instrumentation that performs the applications, functions and procedures for monitoring the internal organ status. The system handler includes a mapping application 152 and a scoring application 154 that together perform the various procedures described herein including mapping electrical properties of an internal organ and thereafter providing a score of the status of the internal organ. The mapping application 152 maps measurements received from each of the plurality of electrodes to provide a graphical representation of the condition of the internal organ, as will be described in greater detail hereinbelow. The scoring application 154 provides a score of the condition, based upon a scale of varying conditions. The score, for example, can be provided as an easily identified scheme, such as a color-coded score, having the colors Green-Yellow-Red, with Green being a normal condition, Yellow indicating a worsened condition, and Red indicating the worst condition, in need of medical treatment. Optionally, the graphical representation (i.e. map) and condition score can be presented, via datastream 155, to a display 160. This can be displayed to a doctor or other clinician to determine the status and condition of a particular internal organ, or to the patient directly. The internal catheter 120 in communication with external electrodes 130 allows for continuous monitoring, mapping, and displaying of the condition of the internal organ (brain 110 in this embodiment).

Figure 2:
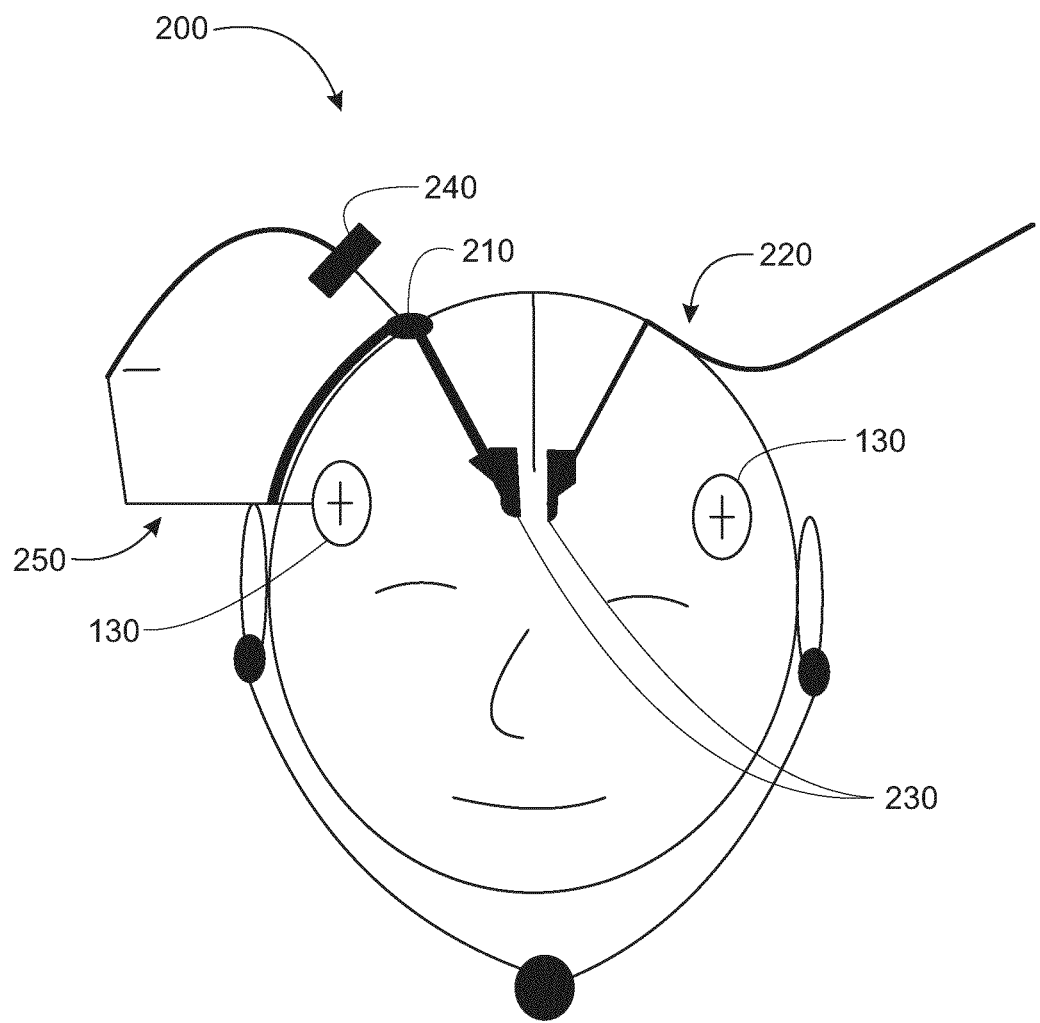
FIG. 2 is a front cross-sectional view of the system for monitoring the brain status, having an implanted shunt and catheter, according to an illustrative embodiment.

FIG. 2 shows a cross-sectional frontal view of an exemplary implementation 200 of the catheter and electrode arrangement in accordance with an illustrative embodiment. As shown, the patient has an implanted shunt 210 and an External Ventricular Drain (EVD) catheter 220 inserted in ventricles 230 of the brain. The shunt 210 has an electrode 240 operatively connected to the shunt 210, such that changes in electrical properties between central electrode 240 and an external electrode 130 can be measured at point 250. A shunt 210 is routinely implanted in a brain for monitoring after a brain injury, to perform functions, such as to relieve pressure within the brain. The shunt 210 provides a pathway for both monitoring and treating intra-cranial edema that arise in these patients. The EVD is an External Ventricular Drain used to relieve pressure, and includes a pressure sensor 222, such as an intra-cranial pressure (ICP) sensor to monitor a brain's internal pressure that can result from swelling of the brain. The pressure sensor in an exemplary embodiment is of the strain gauge type (Codman MicroSensor ICP Transducer MicroSensor Ventricular Catheter Codman, Inc., Raynham, Mass.).

Figure 5A:
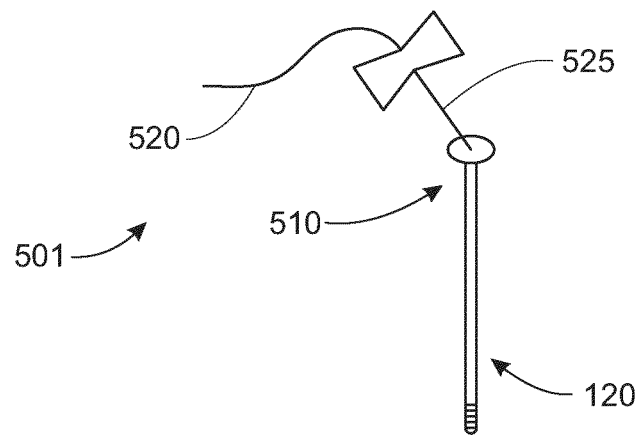
FIG. 5A is a schematic view of an arrangement for the monitoring system, including a shunt and integrated electrode for monitoring the status of an internal organ, according to an illustrative embodiment.
Figure 5B:
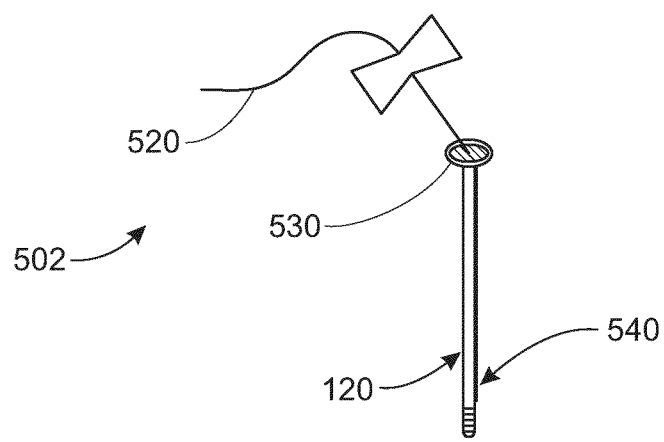
FIG. 5B is a schematic view of another catheter arrangement including a shunt having a side-mounted electrode and a bare wire tip, according to an illustrative embodiment.
Figure 5C:
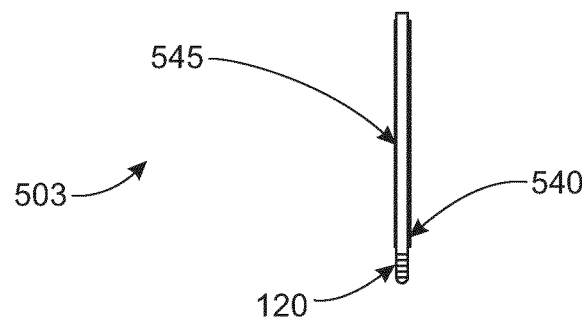
FIG. 5C is a schematic view of still another arrangement for the monitoring system, including a side-mounted electrode and a side-mounted ICP sensor, according to an illustrative embodiment.

There are various techniques for introducing the internal reference electrode and pressure sensor. The internal, central electrode can be defined by the EVD saline pathway with the tapping needle providing the connectivity; the electrode can be defined by the shunt pathway; a side-mounted base wire can serve as the electrode; a separately inserted intraparenchymal base wire electrode can be provided (with or without integrated ICP sensor); and there can be a capacitively coupled high-frequency ICP sensor electrode. The pressure sensor can be directly tapped to the EVD, the shunt reservoir, an Omaya reservoir, or implanted as a stand-alone sensor. The reference electrode measures changing conductivity as a surrogate marker for blood flow within the brain. The intra-cranial electrode provides a significant advantage over other conductivity detection strategies that employ only surface electrodes. FIGS. 5A-5C described in greater detail hereinbelow provide various arrangements and implementations for the intra-cranial electrode.

Figure 3:
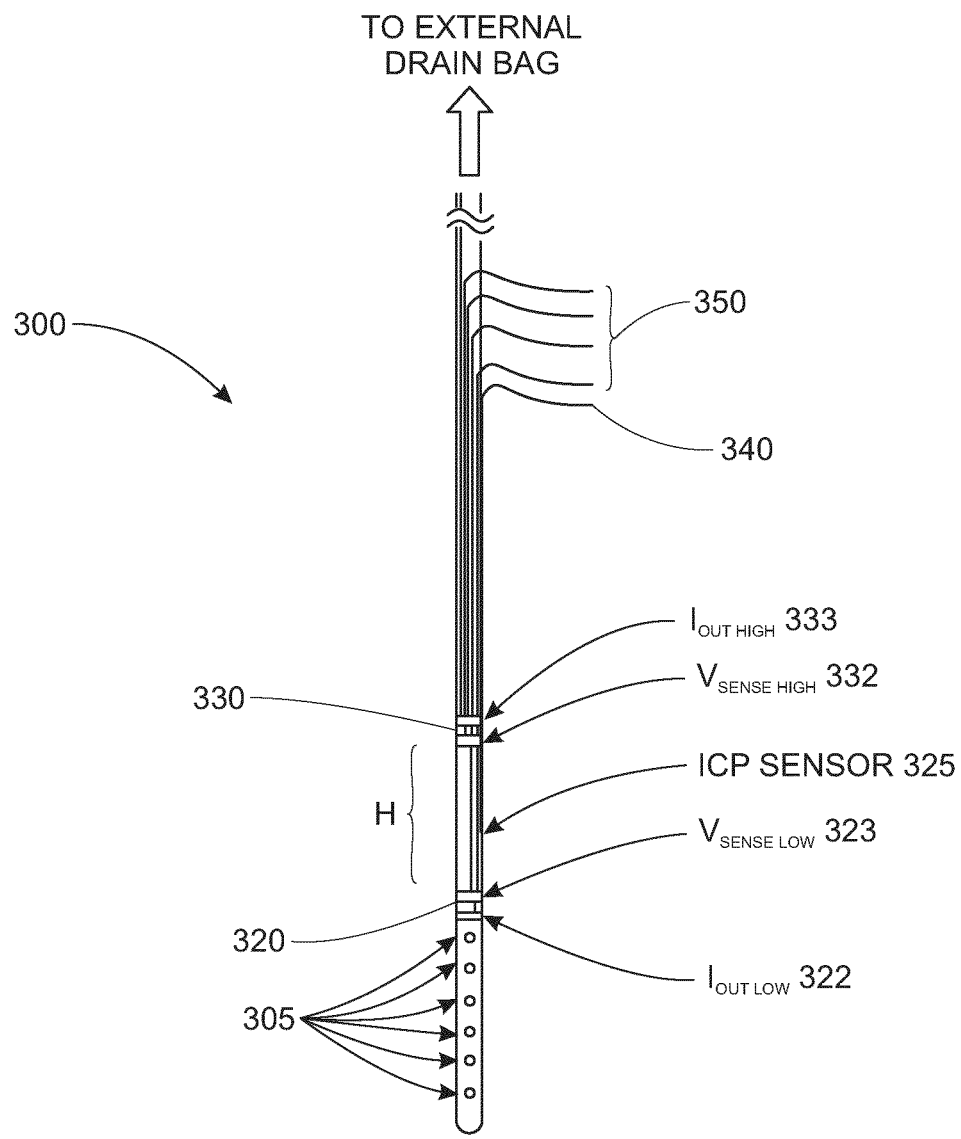
FIG. 3 is a perspective view of an intracranial catheter for the system for monitoring brain status, according to an illustrative embodiment.
Figure 4:
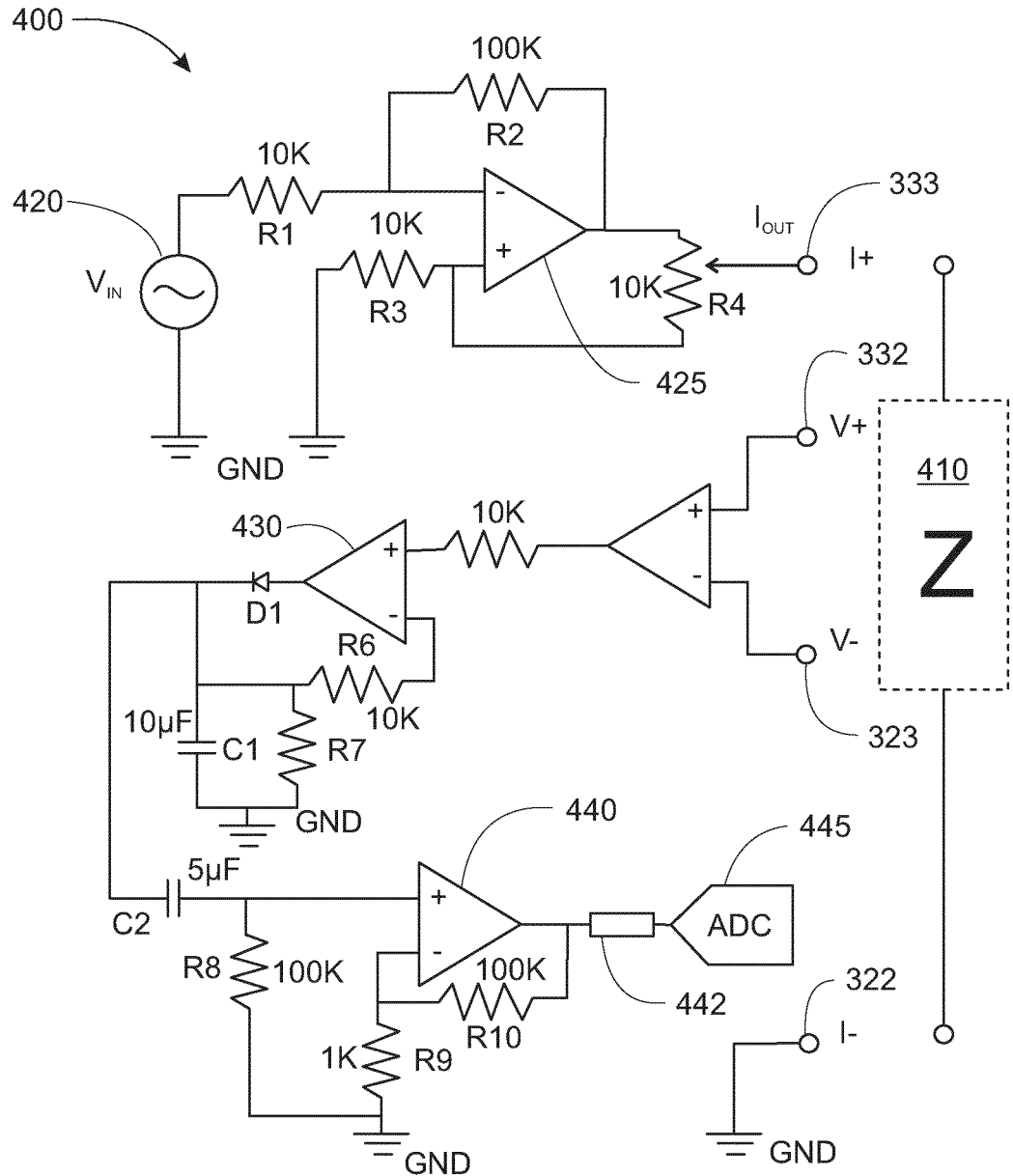
FIG. 4 is a schematic view of an exemplary drive and sense circuit for an internal catheter to measure electrical properties of an internal organ, according to the illustrative embodiments.

An exemplary catheter structure 300 for the monitoring system is shown in FIG. 3, according to an illustrative embodiment. The catheter 300 includes a plurality of apertures 305 in fluid communication with an internal organ, such as the brain 110 of FIG. 1, to allow fluid to drain from the internal organ to relieve pressure. The catheter 300 includes a plurality of measurement locations (322, 323, 332, 333) for measuring the impedance (or other electrical properties) of the internal organ. An exemplary schematic circuit diagram is shown in FIG. 4, and each measurement location is in communication, through a conduit line or other appropriate transmission feed, to an impedance measuring device (see leads 350) or other appropriate instrumentation. The region generally designated 320 is the white matter sense region, and region generally designated 330 is the gray matter sense region. The "white matter sense region" 320 is generally defined as the zone between the cortical gray matter 330 and the lateral ventricle. The white matter sense region 320 is disposed a height 'H' of approximately 4 cm from the gray matter sense region 330 according to an illustrative embodiment. The distance between the white matter sense region 320 and the gray matter sense region 330 can typically range from 3 cm to 6 cm. The $I_{OUT\ LOW}$ 322 and $V_{SENSE\ LOW}$ 323 are disposed generally in the white matter region 320, and the $V_{SENSE\ HIGH}$ 332 and $I_{OUT\ HIGH}$ 333 are disposed generally within the gray matter region 330 to measure an impedance or other electrical characteristic therebetween. This provides the mechanism for measuring impedance of the overall regional internal organ, as the difference in change of intra-cranial pressure from the pressure sensor 325 (operatively connected to a handler or other instrumentation via lead 340) with respect to changes from the impedance circuitry (impedance 410 of FIG. 4).

Reference is now made to FIG. 4, detailing an exemplary circuit diagram 400 in which an impedance ('Z') 410 is measured between a low output, $I_{OUT\ LOW}$ 322 and a $V_{SENSE\ LOW}$ 323, and a high output, $V_{SENSE\ HIGH}$ 332 and $I_{OUT\ HIGH}$ 333. See, for example, catheter 300 shown in FIG. 3. The input signal source 420, $V_{IN}$, is provided through a resistor R1 of 10 k-ohm resistance to the negative terminal of an operational amplifier (op-amp) 425. The op-amp 425 includes a negative feedback resistor R2 of 10 k-ohm resistance. There is provided a $R_{SET}$ resistor R4 of 10 k-ohm resistance, at which the output current is measured ($I_{OUT\ HIGH}$ 333). There is provided a reference current $I_{OUT\ LOW}$ 322 that is grounded, and a $V_{SENSE\ LOW}$ 323 operatively connected to the negative terminal of an inverting amplifier 428, having $V_{SENSE\ HIGH}$ 332 at its positive input terminal. The signal is then driven through a resistor R5 of 10 k-ohm resistance to an op-amp 430. The negative terminal of the op-amp 430 has a negative feedback resistor R6 of 10 k-ohm resistance, operatively connected to the output through a diode D1 and grounded through a capacitor C1 of 10 µF capacitance in parallel with a resistor R7. The resistor R7 serves to bleed some of the stored energy out of the envelope detector. Its value is determined by the demodulated frequency of interest as well as the quality of C1. An exemplary value for R7, assuming an ideal C1 and a demodulating frequency of interest of 10 Hz, can be approximately 1M-ohm resistance. The diode D1 performs signal rectification by passing only positive voltages and is a component of the envelope detection circuit to demodulate the bio-impedance waveform.

The input of the op-amp 440 is driven through a capacitor C2 of 5 µF capacitance and grounded through a resistor R8 of 200 k-ohm resistance. The negative terminal is grounded through a resistor R9 of 1 k-ohm resistance. The op-amp 440 includes a negative feedback resistor R10 of 100 k-ohm resistance. The output of the op-amp 440 is driven through a low-pass filter 442, for use in an illustrative embodiment with an analog-to-digital converter (ADC) 445, or other appropriate instrumentation such as a scope. $I_{OUTLOW}$322 is grounded to provide a reference measurement to determine the impedance 410 of the internal organ.

Note that the circuit values described above are only illustrative, and different values can be employed to achieve similar results. It is also expressly contemplated that a variety of circuits and/or digital processor implementations can be employed to carry out the functions described above within the ambit of ordinary skill.

Figure 9:
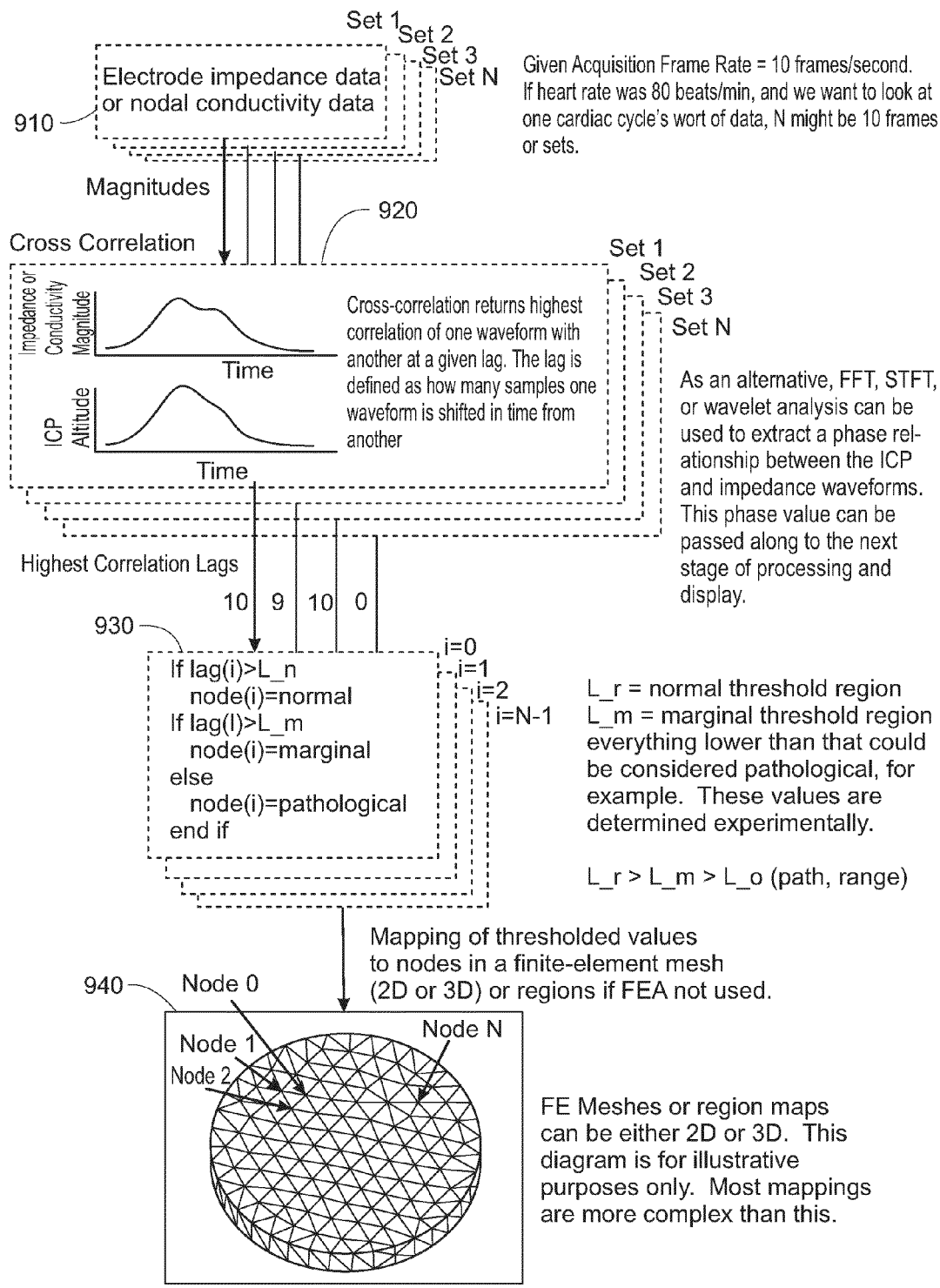
FIG. 9 is a flow diagram detailing a correlation procedure for correlating measurements to determine the condition of an internal organ, according to the illustrative embodiments.

Reference is now made to FIGS. 5A-5C, detailing alternate implementations and arrangements for the placement of a pressure sensor and an internal electrode, both correlated together to provide the impedance and other electrical properties of an internal organ. An exemplary correlation procedure is illustrated in FIG. 9 and described in greater detail hereinbelow. Electrodes are configured as 22-30 gauge tungsten, gold, or stainless steel wire insulated, for example, with a Teflon® coating with 1-5 mm of the wire tip exposed. Alternative high conductivity biocompatible metal electrodes are also contemplated. These electrode leads are typically 4-10 inches long and are embedded alongside a shunting tube or similar catheter such as an external ventricular drain (EVD). A strain-gauge type ICP sensor with a diameter of 1 mm-2 mm is also located alongside the central electrode(s). The ICP sensor can be positioned inside this trocar with the ICP sensing tip located proximate, and just beyond, the trocar tip for pressure sensing. An external ventricular drain is a typically 3 mm OD barium impregnated catheter with a closed proximal tip and a plurality of wall holes at the tip to allow cerebrospinal fluid (CSF) ingress into the lumen and external drainage for control of pressure by drainage of CSF. It is typically inserted through a burr hole in the cranium about 3 cm lateral of the bregma at the vertex of the cranium to a depth of 5-6 cm where it communicates into one of the lateral ventricles. The excess extracranial tubing is tunneled beneath the scalp and connected to an external drain bag. The pressure of the intracranial space can be monitored by transducing the CSF column of the lumen or alternatively a separate pressure transducer attached at the proximal tip or side wall of the intracranial inserted component. The transorgan electrical impedance can be measured by inserting within the lumen a biocompatible electrical wire. Alternatively, the wire can be incorporated in the wall or on the outside of the wall of the catheter such that an exposed tip makes electrical contact with the CSF or organ tissue.

FIG. 5A shows an arrangement 501 wherein a shunt 510 is placed within an internal organ, such as the brain, for monitoring, draining, and performing other functions associated with the treatment and monitoring of a condition of the internal organ. The shunt includes a catheter 120, exemplary of the catheter inserted into the brain 110 of FIG. 1. According to the implementation 501 of FIG. 5A, there is provided an internal electrode 520 directly integral with the shunt 510. There is also provided an integrated pressure sensor 525. The pressure sensor 525 and electrode 520 provide the measurements to determine impedance and other electrical properties of the internal organ. According to this implementation 501, the saline pathway within the catheter serves as the electrode providing a conductive pathway for current flow. In this implementation, the saline electrode is interfaced to external instrumentation through a needle electrode inserted within the catheter.

FIG. 5B shows an arrangement 502, also including a shunt 510. The shunt includes an electrically connected plate 530 in the tapping reservoir. As shown, there is provided a side mounted insulated metallic wire with an exposed tip 540 that acts as the electrode. In this implementation, the implanted wire electrode is interfaced to external instrumentation through a needle electrode contacting the conductive plate 530 within the tapping reservoir. FIG. 5C shows still another arrangement 503, with a wire electrode 540 running along the side of the EVD, in addition to an ICP 545 embedded alongside of the EVD. In such an arrangement, both the ICP and wire-electrode have a long lead protruding from the scalp that can be directly connected to instrumentation. For a comatose patient, this arrangement provides an efficient and robust mechanism for interfacing with these implanted probes.

Figure 6A:
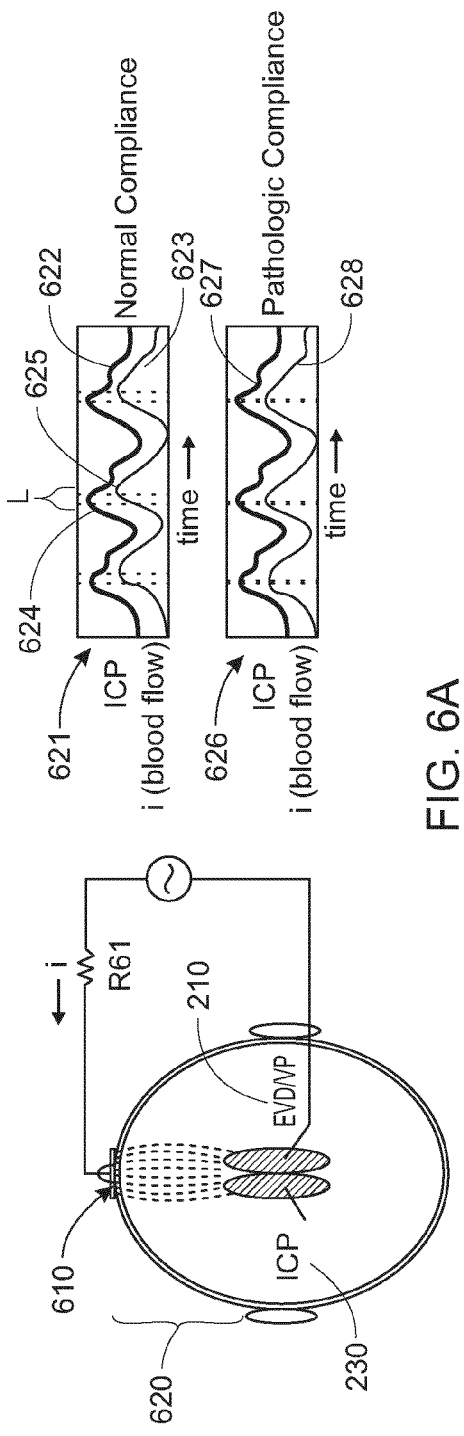
FIG. 6A is a top cross-sectional view of a brain, and corresponding graphical representations, for a system employing a two-electrode configuration for monitoring intra-cranial regional brain compliance, according to an illustrative embodiment.
Figure 6B:
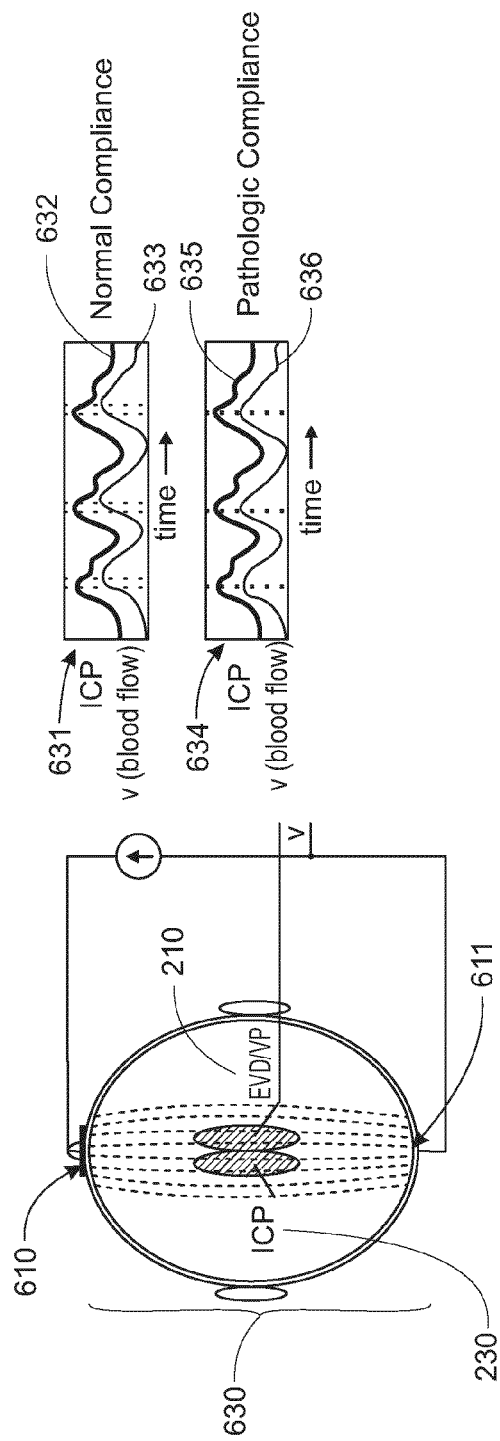
FIG. 6B is a top cross-sectional view of a brain, and corresponding graphical representations, for a system employing a three-electrode configuration for monitoring intra-cranial region brain compliance, according to an illustrative embodiment.
Figure 6C:
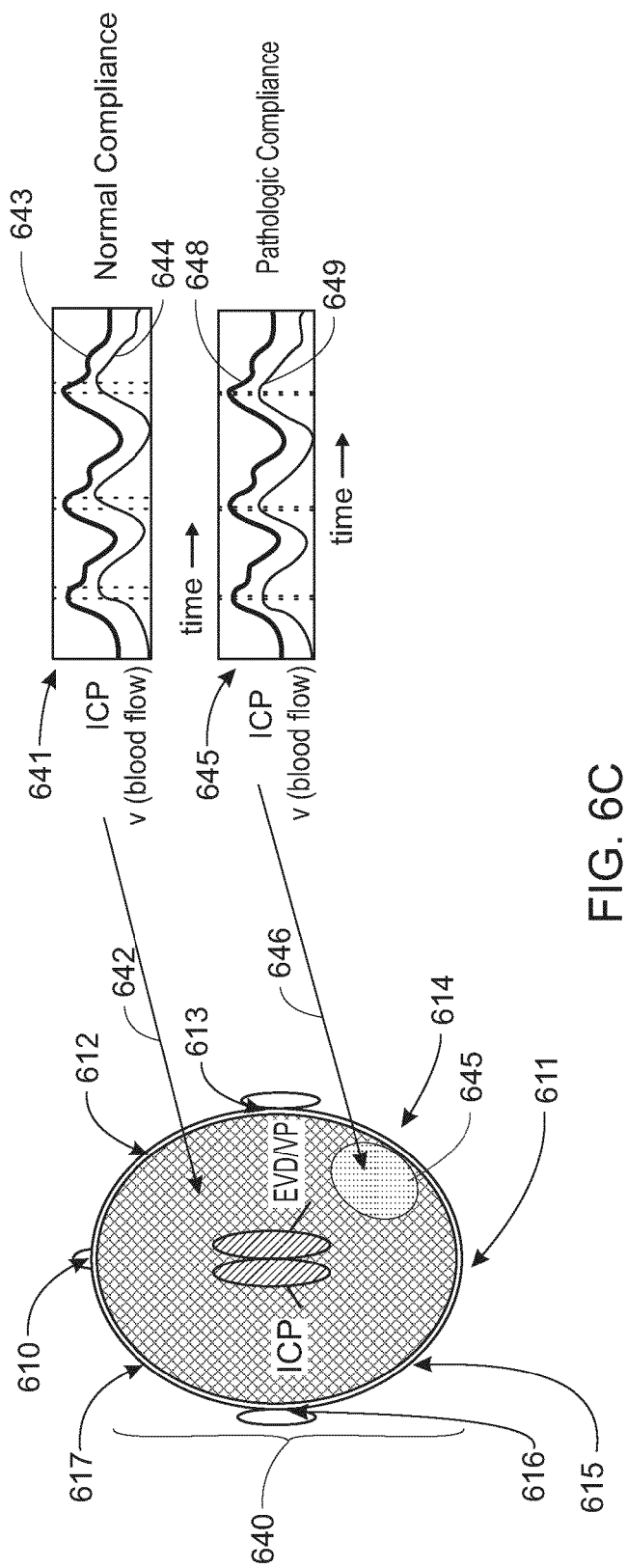
FIG. 6C is a top cross-sectional view of a brain, and corresponding graphical representations, for a system employing a multi-electrode configuration for spatiotemporal imaging and mapping of brain compliance, according to an illustrative embodiment.

Reference is now made to FIGS. 6A to 6C, showing three exemplary implementations and arrangements for an internal electrode and external reference electrode(s) to measure the electrical properties of an internal organ. The corresponding waveforms associated with each implementation are also shown and described. With reference to FIG. 6A, there is provided a two-electrode configuration for monitoring intracranial brain compliance, according to an illustrative embodiment. As shown, there is provided a separate EVD shunt 210 and ICP sensor 230. A reference electrode is coupled to the EVD shunt using one of the mechanisms listed in FIG. 1, 2, 5A, 5B or 5C. The intra-cranial electrode is established as a ground reference according to this implementation of FIG. 6A. A voltage ($V_E$) is applied between the reference electrode at the EVD 210 and an external electrode 610 to interrogate for the intra-cranial conductivity. The dashed lines of region 620 depict the current field established when this voltage differential is applied. The voltage ($V_E$) is established by driving a voltage of a certain magnitude ($V_A$) through a sense resistor (R61) to the surface electrode 610. The current flowing ($I_S$) through the sense resistor is equivalent to the current flowing between the surface electrode 610 and the intra-cranial electrode (at 210) and its value is $([V_A-V_E]/R61)$. The ratio of current to electrode voltage ($I_S/V_E$) represents the bulk conductivity of the region 620 between the two electrodes. Note that there are a number of different circuits that can be used for applying and gauging currents and voltages. The recorded conductivity is a surrogate marker for blood volume and, when measured over time, represents temporal blood flow, shown as lines 623 and 626 in graphs 621 and 624, respectively. These graphs and others described below can be generated using conventional mapping techniques for mapping electrical properties, such as those provided by a conventional oscilloscope for providing a graph of a particular signal, or according to more complex procedures for mapping mesh nodes of a particular region, described in greater detail below with respect to FIG. 9 and its correlation procedure.

FIG. 6A illustrates a normal compliance waveform 621, which includes ICP waveform 622 (obtained from the pressure sensor) and a blood flow (current) waveform 623. In a brain with normal compliance (graphical representation 621), there is a notable temporal lag (L) between the peak 624 of the temporal pressure pattern 622 and the peak 625 of the blood flow waveform 623. As the brain becomes less compliant (a condition associated with worsening pathology and requiring intervention), this lag decreases, as shown in the graphical representation 626. The change in lag is shown in the graphical representations of FIG. 6A, where the representation 621 shows the brain with normal compliance having a lag L between the peak 624 of the ICP waveform 622 and the peak 625 of the blood flow waveform 623. The graphical representation 626 shows the pathological state with the peaks in ICP and blood flow no longer showing the temporal lag. The correlation coefficient between the two waveforms is used as a measure of bulk compliance, for example. A correlation coefficient threshold is used to determine when treatment or intervention should be offered to the patient. Other procedures, which can be used to determine the lag between the waveforms, include the Short Time Fourier Transform (STFT), the Fast Fourier Transform (FFT), and the Wavelet Transform (WT). These operations are easily accomplished by one of ordinary skill.

Reference is made to FIG. 6B, showing a three-electrode configuration for monitoring intracranial brain compliance. In this configuration, current is driven through two surface electrodes, 610 and 611, and the voltage is sensed between the intra-cranial electrode and a ground reference. The field generated between the electrodes is represented by the dashed lines as region 630. In the configuration of FIG. 6B, a fixed current is applied between the surface electrodes 610, 611, independent of any contact impedance, to provide improved temporal stability and a more accurate assessment of intra-cranial changes in blood flow. This implementation further provides for the surface electrodes to be disposed at any location along the surface of the cranium. This provides a mechanism for monitoring a specific region within the cranium. For example, if the trauma was inflicted on the right hemisphere, it is desirable to position one of the surface electrodes anterior to the right ear overlying the temporal lobe of the brain, proximate the region of interest.

The pressure and blood flow are monitored simultaneously through graphical representations 631 and 634. Graphical representation 631 presents normal compliance, and shows the ICP waveform 632, as well as blood flow waveform 633 with a significant lag therebetween. Graphical representation 634 presents pathologic compliance (a worsening condition), and shows the ICP waveform 635 and blood flow waveform 636, having a substantially reduced, if any, lag therebetween.

Electrical Impedance Tomography (EIT)

In FIG. 6C, a spatially distributed map of brain compliance is constructed using Electrical Impedance Tomography (EIT) to assess blood flow and other conditions of the brain. In this configuration, a large number of electrodes (typically 8-64) are placed about the surface of the cranium. Any number of electrodes, from one to the hundreds, is contemplated, FIG. 6C shows eight surface electrodes. At least one intra-cranial electrode (or a plurality of electrodes) with integral pressure sensor is implanted using one of the variations listed above with respect to FIG. 2, or any alternate implementation, readily recognized by those of ordinary skill. Either voltages or currents, depending on the application, are applied to all electrodes (including the intra-cranial electrode) simultaneously, or to a subset of electrodes. The currents and/or voltages are measured at each electrode. The applied voltages (currents) and measured currents (voltages) are input to a mathematical procedure, for example a correlation procedure such as that shown in FIG. 9, for mapping the electrical properties, described in greater detail hereinbelow. Conductivity distribution within the brain can be mapped from a procedure that computes the electrical properties based upon measured quantities of voltage and/or current. Typically, numerical methods such as Finite Element Models (FEM) are used to reconstruct these maps. In FEM, a mesh is generated from a span of connected spatially distributed nodes. These connections form, as an example, triangles in a two-dimensional domain (shown in FIG. 6C and described in the flow chart of FIG. 9), or as a tetrahedron in a three-dimensional domain according to an alternate embodiment. The conductivity, or blood flow, is calculated at each of these nodes. This mapping can occur in real-time to provide a map of blood flow (see individual frames 710 in FIG. 7, for example). A correlation coefficient is calculated between the temporal blood flow and the ICP waveform at each mesh node (see procedure 900 of FIG. 9). These correlation coefficients are then displayed on the FEM mesh and provide a surrogate map of brain compliance. As shown in FIG. 6C, a region of poor compliance is illustrated at 647, and represented in a graphical representation 645 corresponding to (arrow 646) the poor compliance region 647. The graphical representations 641, 643 show the pressure and blood flow for at least two different regions of the brain (arrows 642, 644). The graphical representations display the brain compliance (correlation coefficients), as determined at each node based on these temporal waveforms.

Referring to FIG. 6C, a multi-electrode configuration is provided for monitoring intracranial brain compliance. In this configuration, a signal is driven through multiple surface electrodes (610, 611, 612, 613, 614, 615, 616, and 617). The voltage is sensed between the intra-cranial electrode and a ground reference. The normal compliance is shown in the graphical representation 641, showing a pressure waveform 643 and blood flow waveform 644. Note the lag present for normal compliance, representative of a normal region of interest, shown by arrow 642. The pathologic compliance is shown in the graphical representation 645, corresponding to (arrow 646) a worsened region of interest 647. In the graphical representation 645, there is no lag between the pressure waveform 648 and blood flow waveform 649.

Figure 7:
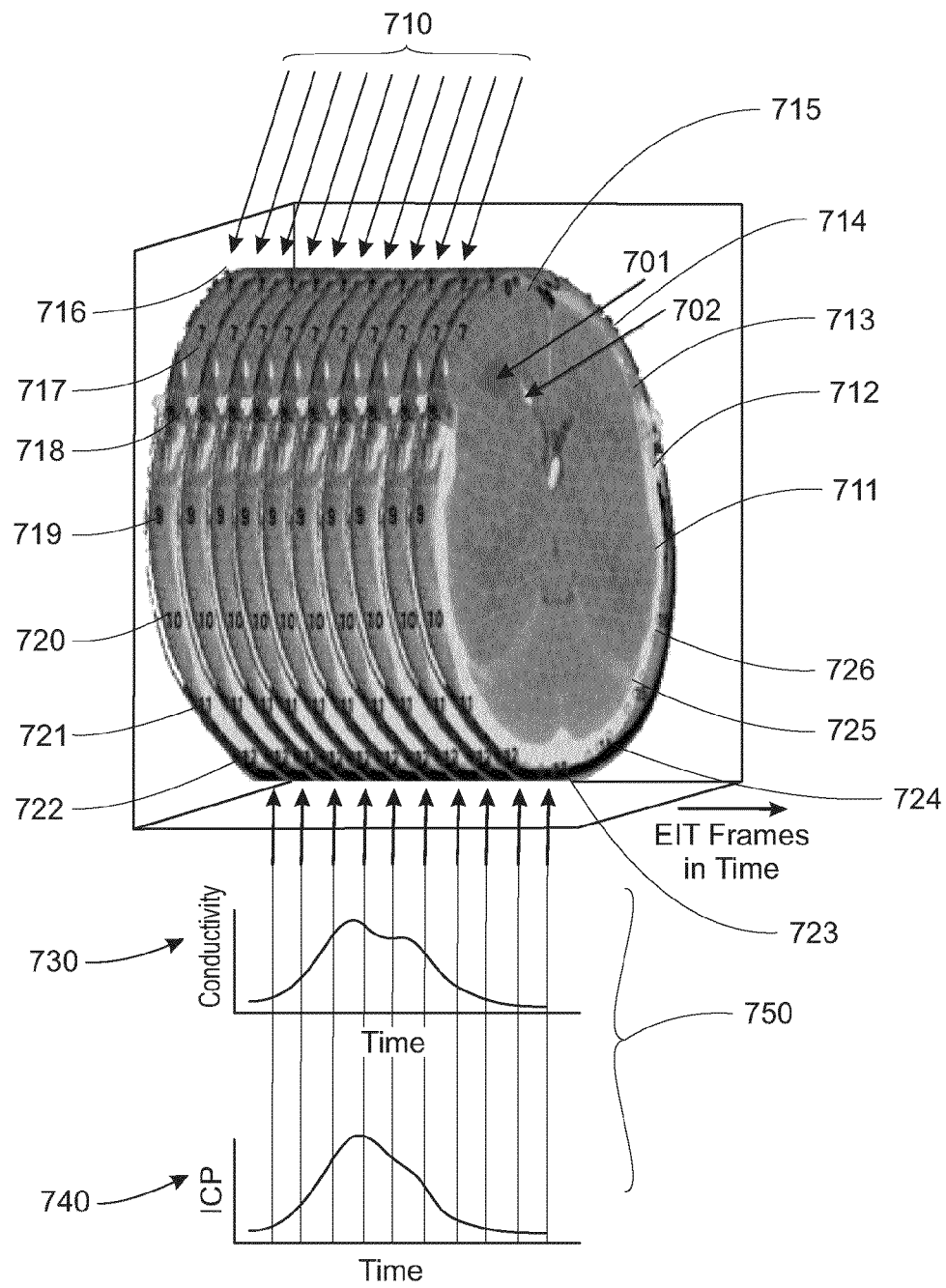
FIG. 7 is a perspective view of a plurality of discrete image frames and corresponding compliance maps for the system for monitoring the status of an internal organ, according to the illustrative embodiments.

FIG. 7 shows a continuous monitoring of a brain, through a plurality of tomographic maps 710 constructed by performing EIT. There is a plurality of frames or segments 710, that each represents a map of one instance in time, and together show a continuous status of a brain. A region of interest 701 can be observed using a pressure sensor 702. A plurality of external sensors 711, 712, 713, 714, 715, 716, 717, 718, 719, 720, 721, 722, 723, 724, 725 and 726 (sixteen surface electrodes in this embodiment) are provided to measure the electrical properties, and thus overall condition, of the brain. The frames 710 each correspond to a point in time, as represented by the graphical representation 730 for conductivity and graphical representation 740 for ICP. As shown, there is a lag between the peak of conductivity and the peak of pressure, indicating normal brain compliance for the particular region of interest. The cross-correlation between the conductivity and pressure 750 determines the phase shift, and accordingly changes in status of the brain.

Figure 8:
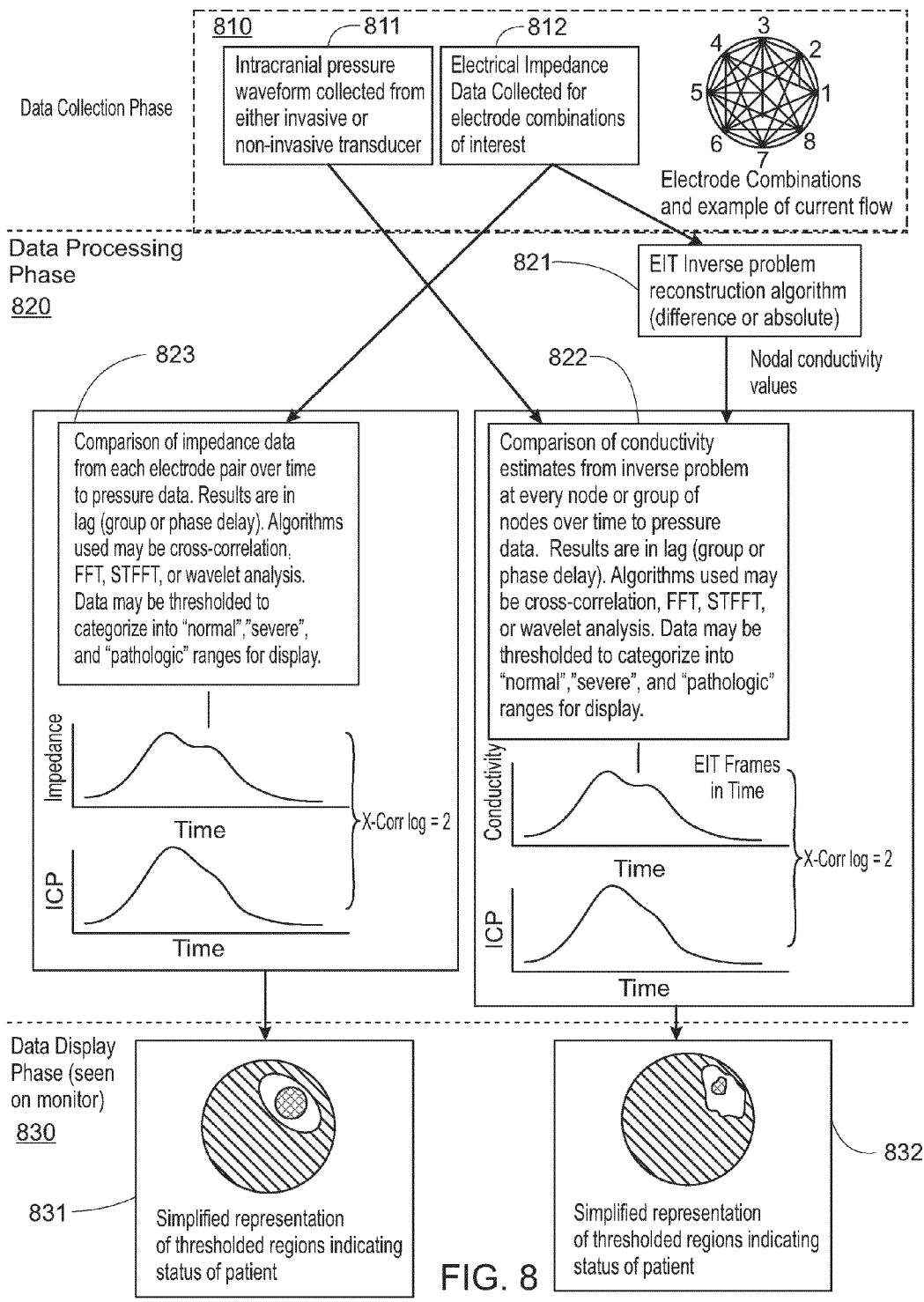
FIG. 8 is a flow diagram detailing the steps for performing the monitoring of the condition of an internal organ, according to the illustrative embodiments.

Reference is now made to FIG. 8, showing an overview block diagram for the system procedure 800 for performing the monitoring of the condition of an internal organ, according to the illustrative embodiments. The procedure 800 defines a data collection phase 810, a data processing phase 820 and a data display phase 830. In the data collection phase 810, at step 811 the intracranial pressure waveform is collected from a transducer. At step 812 of the data collection phase 810, the electrical impedance is collected for electrode combinations of interest. These combinations represent a region of interest for determining blood flow through monitored and measured electrical impedance.

In the data processing phase 820 of procedure 800, at step 821, the electrical impedance values are run through an EIT Inverse problem reconstruction procedure. This procedure determines the difference or absolute of the impedance value to provide a positive real number for comparison at step 822. At step 822, comparison of conductivity estimates are performed from inverse problem at every node, or group of nodes, over time to pressure data. These results are in lag, including group lag or phase delay. The comparison of conductivity estimates can be performed according to any number of procedures to provide a mapping of data, such as cross-correlation (described in detail with respect to FIG. 9), FFT (Fast Fourier Transform), STFT (Short-Time Fourier Transform), or wavelet analysis. The data can be assigned a threshold for each category, to appropriately divide the correlated data into "normal", "severe" or "pathologic" ranges for the display.

At step 823 of the data processing phase 820, a comparison of impedance data is performed from each electrode pair over time to the pressure data. Results are provided in lag, either group or phase delay. The same procedures for comparing conductivity data are applicable to comparing the impedance data. These procedures include cross-correlation (see, for example, FIG. 9), FFT, STFT, or wavelet analysis. This data can also be thresholded to categorize into "normal", "severe", and/or "pathologic" ranges for the display.

In data display phase 830, at step 831 and 832, the threshold regions (i.e. normal, severe and pathologic) are provided in a graphical representation, indicating the status of a patient. The graphical representation provides a tomographic image of the brain or map of the condition of the brain and the various regions within the brain.

FIG. 9 details an exemplary procedure 900 for a correlation procedure that is employed to correlate the gathered data. At step 910, a plurality of "sets", or frames, of the brain are gathered, either as electrode impedance data or nodal conductivity data. Cross-correlation is performed at step 920, which returns the highest correlation of one waveform with another at a given lag. This lag is defined as how many samples one waveform is shifted in time from another waveform. As an alternative, FFT, STFT, or wavelet analysis can be used to extract a phase relationship between the ICP (pressure) and impedance waveforms. This phase value can be passed along to the next stage of processing and display.

At step 930, the procedure 900 assigns the lag with a value, or category, corresponding to the condition, for example "normal", "marginal", or "pathological". Then at step 940, each value is mapped and each node, or region of interest, is given the category corresponding to the condition, to provide the graphical representation at 940. The mapping of threshold values to the nodes (N0, N1, N2, ..., NN) is performed in a finite-element (FE) mesh, two-dimensional or three-dimensional. Or if FE mesh mapping is not used, the values are mapped into regions. The FE meshes or region maps can be either two-dimensional or three-dimensional. The mapping at step 940 is one exemplary mapping, and can be significantly more complex in alternate embodiments.

Figure 10:
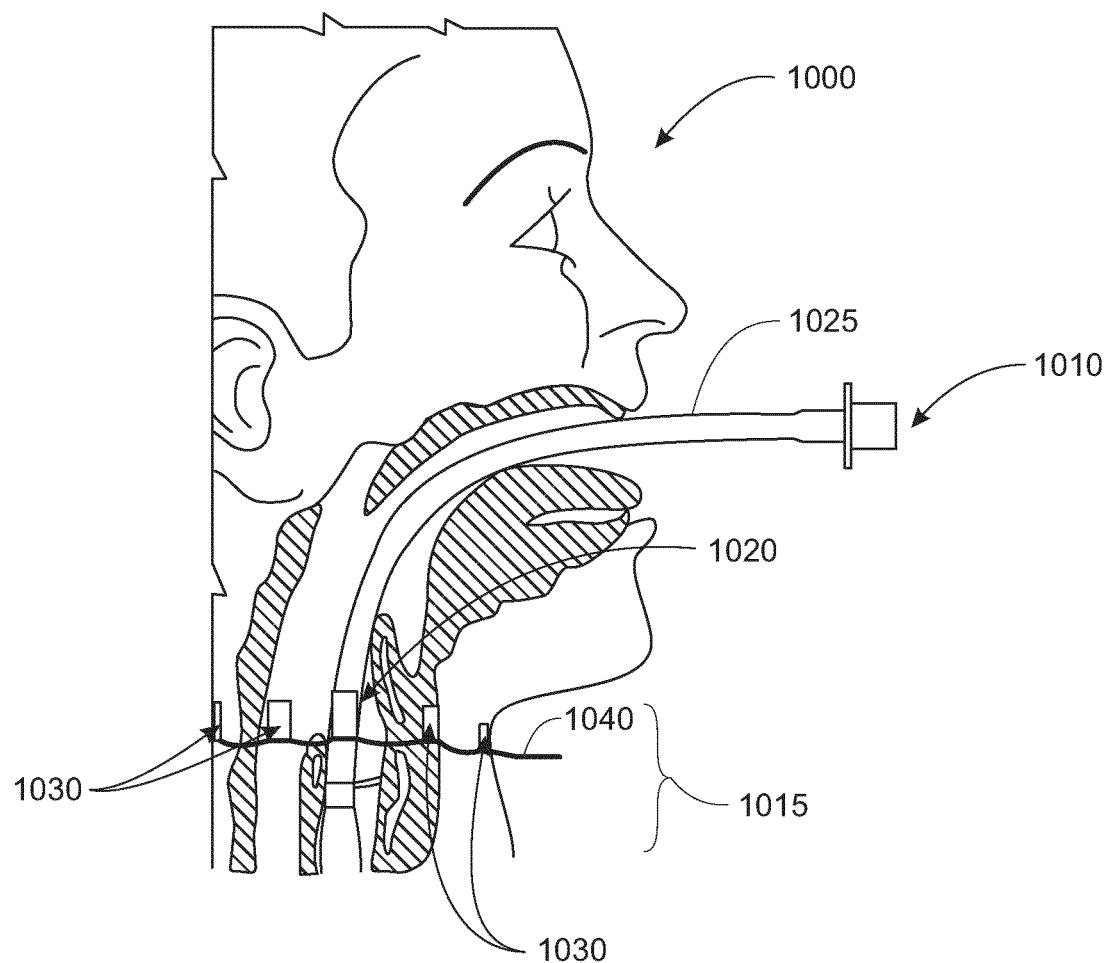
FIG. 10 is a schematic view of an alternate implementation of the system for monitoring the status of an internal organ, showing a side cross-sectional view of an internal electrode arrangement, according to an alternate embodiment for monitoring a trachea.

Having described illustrative arrangements and procedures for monitoring the brain, reference is now made to FIG. 10, which describes the implementation of the monitoring arrangement contemplated herein with another internal organ—in this example, the tracheal region of the body. FIG. 10 shows a tracheal monitoring system for a patient 1000. A conventional endotracheal tube 1010 is provided for monitoring a tracheal region 1015. The tube 1010 includes an internal electrode 1020 with lead 1025 for monitoring the region 1015 in this illustrative embodiment, according to the systems and methods described herein. The system of FIG. 10 includes a plurality of exterior, surface, electrodes 1030 for monitoring the region. The electrodes 1030 are operatively connected to a system handler (cable 1040). The electrodes can each be operatively connected to the system handler through one cable or through wireless or any other appropriate transmission means. This system arrangement allows for continual monitoring of the tracheal region 1015 with the central electrode to provide real-time status of the condition of the region. Such monitoring allows the continuous assessment of perfusional symmetry of the carotid arteries, of interest during the management of carotid insufficiency and risk of stroke. Similar configurations about other organs and body regions based on these principles include the chest with a central bronchial or esophageal electrode for chest compliance monitoring; the prostate with a central electrode within the urethra for assessment and treatment of prostatic hypertrophy or tumor; the gravid uterus with a central vaginal electrode for assessment of fetal perfusional sufficiency and heart rate. Yet other applications based on these principles are readily apparent to those familiar with the art.

Figure 11:
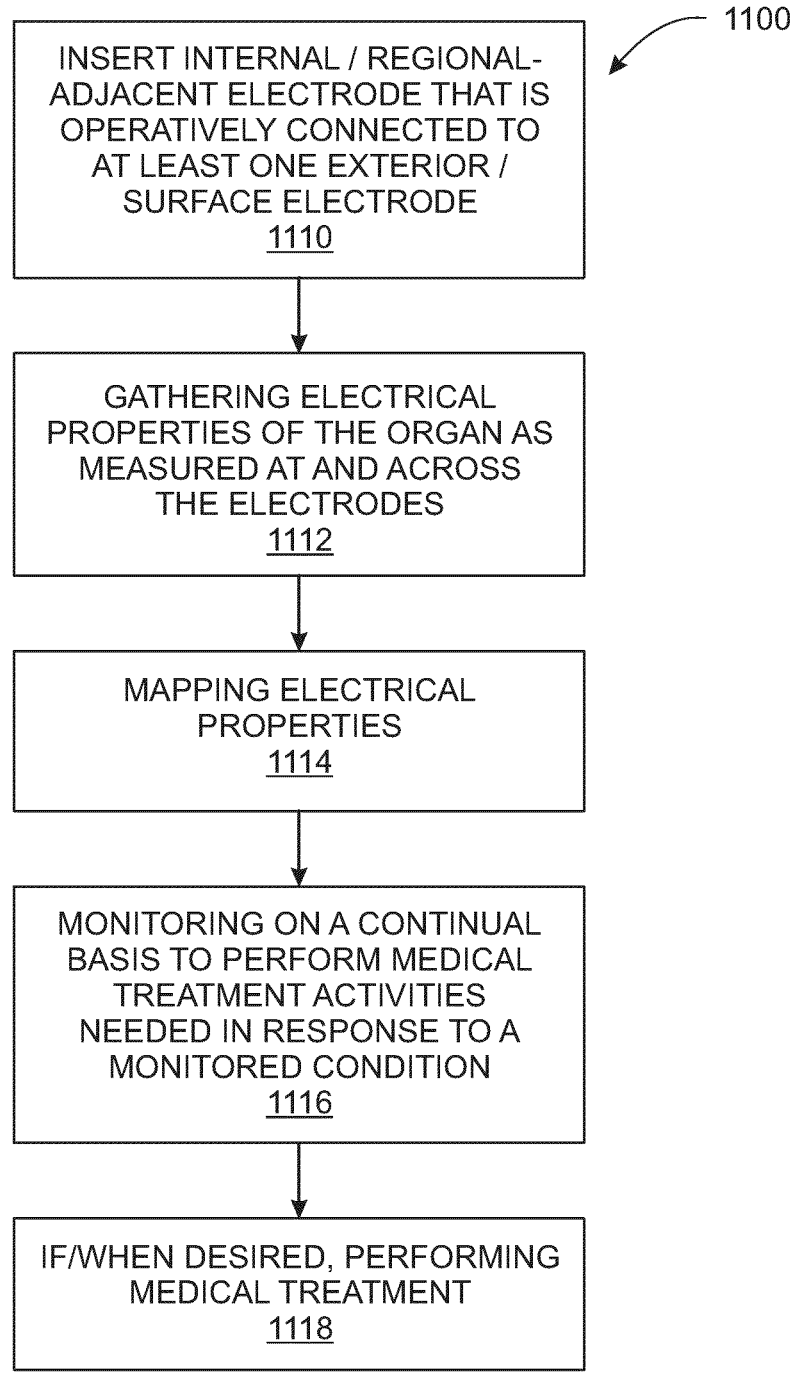
FIG. 11 is a generalized flow diagram of a medical treatment procedure employing the monitoring arrangement according to an illustrative embodiment with respect to a predetermined internal organ or region.

FIG. 11 is a generalized flow diagram of a medical treatment procedure employing the monitoring arrangement according to an illustrative embodiment with respect to a predetermined internal organ or region. The procedure 1100 begins at step 1110 with the insertion of an internal electrode, or regional-adjacent electrode, which is operatively connected to at least one exterior (surface) electrode. The internal electrode is provided to measure overall electrical properties of the organ or region of interest with respect to a plurality of surface electrodes, in accordance with the embodiments described herein. At step 1112, the procedure 1100 then gathers data of the electrical properties of the organ as measured at and across the electrodes. These electrical properties are then mapped at step 1114 according to conventional graphical representation instrumentation (e.g. an oscilloscope) or complex mapping procedures, such as those described herein.

The procedure 1100 then performs monitoring on a continual basis to provide medical treatment activities, as needed, in response to a monitored condition. This allows a physician to perform a particular treatment quickly and efficiently in response to the monitored conditions of the organ. The procedure then terminates at step 1118 when the medical treatment is performed, if and/or when desired.

Figure 12:
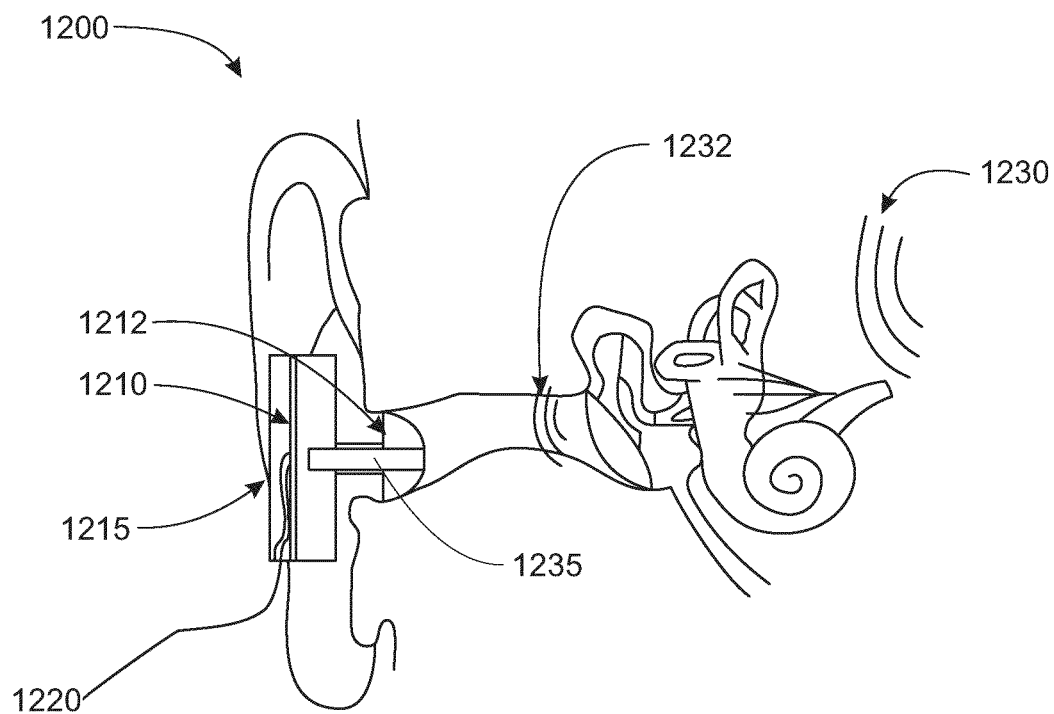
FIG. 12 is a side cross-sectional view of an exemplary patient's head depicting a non-invasive embodiment of the system for monitoring internal pressure according to this invention located with respect to the ear canal and tympanic membrane.

Reference is now made to FIG. 12 detailing a non-invasive system 1200 for monitoring an internal organ. By "non-invasive", it is meant that an internal, invasive (i.e. penetrating) electrode is not employed. Instead, a non-invasive sensing element 1210 is provided for obtaining a pressure waveform for comparison to an impedance waveform to perform the monitoring and mapping of an internal organ. This non-invasive system employs a procedure for invading a cavity of a person by creating a pathway through tissue, which is free of internal penetration and physical invasion into a bodily cavity.

In this non-invasive system, there is provided a non-invasive sensing element 1210 that is operatively connected to an air-tight earpiece 1212. The sensing element is disposed within an enclosure 1215 that can be plastic or any other suitable material. The exemplary sensing element 1210 is a low-frequency (0.01-20 Hz) high-sensitivity piezo infrasonic sensing element, according to an illustrative embodiment. In alternate embodiments, the sensing element can employ a different modality to detect pressure. For example, a laser-based system can be alternatively employed. It is contemplated that the "sensing element" as defined in this illustrative embodiment can be any device that attains a pressure reading using the general device placement shown herein. The sensing element 1210 is operatively connected to an amplifier and data acquisition hardware via cable 1220. The sensing element is capable of sensing changes in intracranial pressure. The intracranial pressure pulses push on the inner ear (arrow 1230). The infrasonic intracranial pressure waves are generated from the ear drum (arrow 1232) such that they are "capacitively" coupled through the air column 1235 to the sensing element 1210. This provides an accurate intracranial pressure waveform morphology for comparison to the flow (impedance) waveform according to the procedures described herein.

It should be clear from the above description that the system and method provided herein affords a relatively straightforward, non-injurious, accurate and continuous mechanism for monitoring an internal region of the body. The internal region may cover any internal organ or similar structure, as well as a particular organ being monitored or assessed for a condition or particular injury. The various materials and arrangements of materials should be readily apparent to those of ordinary skill.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the recitations herein have been described and illustrated variously with respect to a brain. However, the teachings are readily applicable to any internal organ, and should be apparent to one of ordinary skill. While "organ" is used, this should be taken broadly to include a plurality of adjacent internal structures (e.g. muscles, arteries, tissues) that can be monitored as a discrete internal "region". Moreover it is expressly contemplated that the methods and processes described herein can be implemented using electronic hardware, software consisting of a computer/processor-readable medium containing program instructions or a combination of hardware and software. Accordingly, this description is meant to be taken only by way of example, and not to otherwise limit the scope of this invention.

What is claimed is:

1. A system for monitoring a state of a brain, the system comprising:
   at least one internal electrode constructed and arranged to be placed adjacent to at least a portion of the brain and in communication with a system handler to provide a measurement thereto of electrical properties of the brain;
   the internal electrode being provided on an intracranial catheter that is constructed and arranged to be placed within the brain to monitor a condition of the brain as a measurement of electrical properties thereof;
   an intracranial pressure sensor for monitoring intracranial pressure within the brain by providing a measurement of pressure of the brain; and
   at least one exterior electrode placed proximate and exterior to the at least one internal electrode to generate a signal therebetween in order to return a state of blood flow-induced electrical properties of the brain, such that the electrical properties of the brain indicate the blood flow-induced status of the brain;
   wherein the status of the brain is determine by performing a group delay or phase shift analysis between the measurement of pressure of the brain and the state of blood flow-induced electrical properties of the brain.

2. The system as set forth in claim 1 further comprising a second exterior electrode in communication with the at least one internal electrode and the system handler to determine the electrical properties of the brain.

3. The system as set forth in claim 1 wherein the system handler comprises instrumentation for measuring and mapping the electrical properties of the brain.

4. The system as set forth in claim 1 further comprising a plurality of internal electrodes for measuring the electrical properties of the brain.

5. The system as set forth in claim 1 wherein the intracranial catheter is inserted into a shunt in the brain of a patient such that a saline pathway formed by the shunt provides a conductive pathway for the current to flow between the electrodes.

6. The system as set forth in claim 1 wherein the intracranial electrode is provided as a side-mounted insulated lead with an exposed tip that serves as the intracranial electrode, which is interfaced with the system handler through a needle electrode containing a conductive plate within a tapping reservoir of the intracranial catheter.

7. The system as set forth in claim 1 wherein the electrical properties include a measurement of pressure within a region of interest of the brain, and the group delay of phase shift analysis is performed to provide the state of mechanical properties of the brain by correlating group delay or phase shift of the intra-cranial pressure and the blood flow-induced electrical property changes within a region of interest in the brain.

8. The system as set forth in claim 1 wherein the electrode measures electrical properties within a white matter region of the brain and a gray matter region of the brain.

9. The system as set forth in claim 1 wherein the electrical properties include impedance measured across an internal electrode and the at least one exterior electrode.

10. The system as set forth in claim 1 further comprising a display for displaying the status of the internal organ based upon the state of electrical properties of the internal organ, as thresholded into one of a plurality of predetermined categories.

11. The system as set forth in claim 7 wherein the group delay or phase shift analysis is performed by one of: cross-correlation, FFT (Fast Fourier Transform), STFT (Short-Time Fourier Transform) or wavelet analysis.

12. A system for monitoring a status of a brain, the system comprising:
   a system handler that includes a mapping application and a scoring application that together map electrical properties of the brain and thereafter providing a score of the status of the brain;
   at least one internal electrode constructed and arranged to be placed adjacent to at least a portion of the brain and in communication with the system handler to provide a measurement thereto of electrical properties of the brain;

at least one exterior electrode placed proximate and exterior to the at least one internal electrode to generate a signal therebetween in order to return a state of electrical properties of the brain, the state of the electrical properties of the brain indicating the status of the brain;

the mapping application constructed and arranged to map electrical property lags in measurements of electrical properties of the brain to provide a graphical representation of the status of the brain including a group delay or phase shift analysis performed to provide the status of the brain by correlating intracranial pressure of the brain and blood flow, or a surrogate of blood flow as determined by flow-induced electrical properties of the brain, the graphical representation including a display of threshold regions that indicate the status of the brain; and the scoring application providing the score of the status of the brain based upon a scale of varying conditions.

13. A system for monitoring a status of an internal organ, the system comprising:

at least one internal electrode constructed and arranged to be placed adjacent to at least a portion of the internal organ;

at least one exterior electrode constructed and arranged to be placed proximate and exterior to the at least one internal electrode to generate a signal therebetween in order to return a state of electrical properties of the internal organ, the electrical properties of the internal organ indicating the status of the internal organ; and a system handler constructed and arranged to:

a) gather the electrical properties of the internal organ;

b) perform a group delay or phase shift analysis between the changing electrical properties of the internal organ representing blood flow and changing intra-organ pressure to determine a lag therebetween within a region of interest in the internal organ;

c) assign a score value corresponding to the status of the internal organ; and d) map the score value and corresponding region of interest to a category to provide a graphical representation of the status of the internal organ.

14. The system as set forth in claim 13 wherein the group delay or phase shift analysis is performed by one of: cross-correlation, FFT (Fast Fourier Transform), STFT (Short-Time Fourier Transform) or wavelet analysis.

15. The system as set forth in claim 1 wherein the status of the brain is determined by performing the group delay or phase shift analysis between a peak in magnitude of the measurement of pressure in the brain and a peak in magnitude of the state of blood flow-induced electrical properties of the brain.

16. The system as set forth in claim 12 wherein the group delay or phase shift analysis is performed by correlating group delay or phase shift between a peak in magnitude of intracranial pressure of the brain and a peak in magnitude of the blood flow-induced electrical properties of the brain.

17. The system as set forth in claim 13 wherein the group delay or phase shift analysis is performed by measuring between peaks in magnitude of the electrical properties of the internal organ representing blood flow and pressure.

* * * * *